(12) United States Patent
Duncan

(10) Patent No.: US 8,459,991 B2
(45) Date of Patent: Jun. 11, 2013

(54) ORAL IMPLANT PLACEMENT SYSTEM AND METHOD

(75) Inventor: Gary A. Duncan, Dublin, OH (US)

(73) Assignee: Immediate Implant Technologies, LLC, Dublin (IE)

( * ) Notice: Subject to any disclaimer, the term of this patent is extended or adjusted under 35 U.S.C. 154(b) by 0 days.

(21) Appl. No.: 13/342,134

(22) Filed: Jan. 2, 2012

(65) Prior Publication Data

US 2012/0148982 A1 Jun. 14, 2012

Related U.S. Application Data

(60) Division of application No. 12/428,450, filed on Apr. 22, 2009, now Pat. No. 8,087,934, which is a continuation-in-part of application No. 12/148,996, filed on Apr. 24, 2008, now abandoned, and a continuation-in-part of application No. 11/807,360, filed on May 29, 2007, now abandoned, and a continuation-in-part of application No. 11/807,366, filed on May 29, 2007, now abandoned, and a continuation-in-part of application No. 11/807,377, filed on May 29, 2007, now abandoned, and a continuation-in-part of application No. 11/975,586, filed on Oct. 22, 2007, now abandoned.

(51) Int. Cl.
*A61C 19/04* (2006.01)
*A61C 3/00* (2006.01)

(52) U.S. Cl.
USPC ............................................. 433/72; 433/75

(58) Field of Classification Search
USPC .... 433/72, 76, 172–176, 50, 53, 215; 606/80, 606/96
See application file for complete search history.

(56) References Cited

U.S. PATENT DOCUMENTS 4,023,275 A * 5/1977 Marshall ......................... 433/50
4,802,846 A 2/1989 Posca
(Continued)

FOREIGN PATENT DOCUMENTS

DE 19709215 A1 9/1998
EP 1709929 A1 10/2006
(Continued)

OTHER PUBLICATIONS

Marchack C B. "An immediately loaded CAD/CAM-guided definitive prosthesis: A clinical report", Journal of Prosthetic Dentistry, Elsevier Amsterdam, NL, vol. 93, No. 1, Jan. 1, 2005, pp. 8-12.

(Continued)

*Primary Examiner* — Yogesh Patel
(74) *Attorney, Agent, or Firm* — James R. Eley; Michael A. Forhan; Eley Law Firm Co. LPA

(57) ABSTRACT

An oral implant system and method. The system includes a positioning tool, a transfer band, a transfer screw, and a transfer drill to provide for accurate placement of a dental implant parallel to other implants and or existing teeth and at predetermined depths. A model is made of the patient's maxilla and mandible. The model is marked for implant position, depth and size. Holes are drilled in the model for implant analogs using the positioning tool. The analogs are installed into the model using the positioning tool and a surveyor. Transfer bands are coupled to the analogs and a surgical stent portion is fabricated. The surgical stent is fitted to the patient's occlusion, secured, and then utilized to accurately drill apertures into the patient's maxilla or mandible. The implants are installed into the apertures and the surgical stent is removed. A final restoration is secured to the implants.

16 Claims, 15 Drawing Sheets

U.S. PATENT DOCUMENTS

| | | |
|---|---|---|
| 5,725,376 A | 3/1998 | Poirer |
| 5,769,636 A | 6/1998 | Di Sario |
| 5,797,741 A * | 8/1998 | Bonpard et al. ............... 433/75 |
| 5,989,025 A | 11/1999 | Conley |
| 6,315,563 B1 | 11/2001 | Sager |
| 6,997,707 B2 * | 2/2006 | Germanier ................... 433/75 |
| 7,572,125 B2 | 8/2009 | Brajnovic |
| 2002/0031747 A1 | 3/2002 | Laster et al. |
| 2002/0045731 A1 * | 4/2002 | Schaffer et al. ............ 530/303 |
| 2004/0063062 A1 | 4/2004 | Brajnovic |
| 2004/0219478 A1 | 11/2004 | Harter |
| 2004/0219480 A1 * | 11/2004 | Malin ............................ 433/75 |
| 2008/0064005 A1 | 3/2008 | Meitner |
| 2009/0011382 A1 * | 1/2009 | Bavar ............................ 433/76 |
| 2009/0123887 A1 * | 5/2009 | Brajnovic ..................... 433/75 |
| 2010/0087829 A1 | 4/2010 | Metzger et al. |
| 2010/0151412 A1 * | 6/2010 | Suter et al. .................... 433/75 |

FOREIGN PATENT DOCUMENTS

| | | |
|---|---|---|
| EP | 1759658 A1 | 3/2007 |
| WO | 2007112977 A1 | 10/2007 |

OTHER PUBLICATIONS

Cehreli et al. "Bilaminar dual-purpose stent for placement of dental implants", Journal of Prosthetic Dentistry, vol. 84, 2000, pp. 55-58.

International Search Report and Written Opinion, PCT Patent Application No. PCT/US2009/041517, Jun. 11, 2009.

Extended European Search Report, European Patent Application No. 09734172.1, Mar. 23, 2012.

* cited by examiner

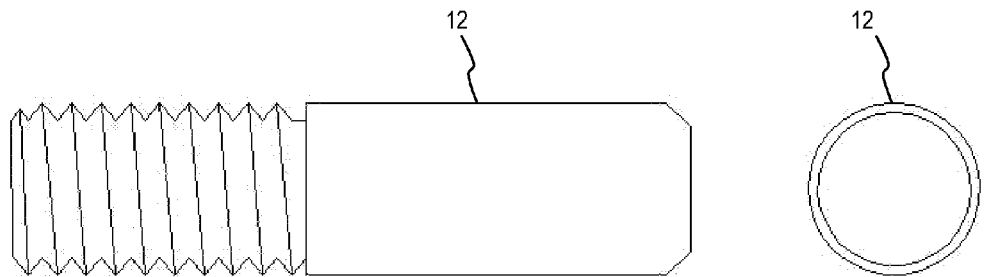
*Fig. 3A*  *Fig. 3B*
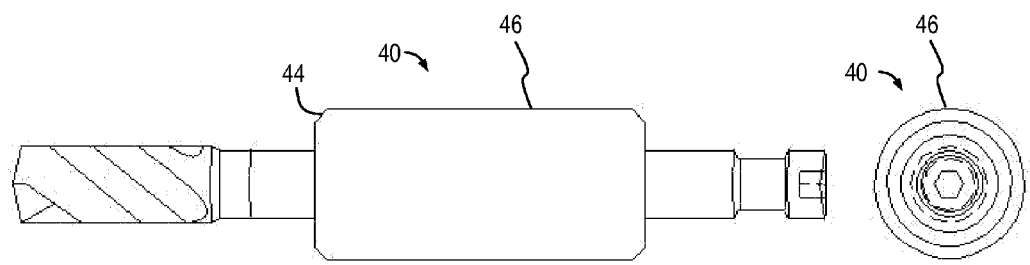
*Fig. 12A*  *Fig. 12B*

ORAL IMPLANT PLACEMENT SYSTEM AND METHOD

This application is a divisional of U.S. patent application Ser. No. 12/428,450, now U.S. Pat. No. 8,087,934, filed Apr. 22, 2009, which is a continuation-in-part of U.S. patent application Ser. No. 12/148,996, filed Apr. 24, 2008, now abandoned; U.S. patent application Ser. No. 11/807,360, filed May 29, 2007, now abandoned; U.S. patent application Ser. No. 11/807, 366, filed May 29, 2007, now abandoned; U.S. patent application Ser. No. 11/807, 377, filed May 29, 2007, now abandoned; and U.S. patent application Ser. No. 11/975,586, filed October 22, 2007, now abandoned. The entire contents of each of these applications is expressly incorporated herein by reference thereto.

FIELD

The present invention relates generally to dental implants, in particular to a system and method for positioning and installing dental implants in a patient's mouth.

BACKGROUND

Teeth are lost for a variety reasons, such as tooth decay, root canal failure, periodontitis (gum disease), trauma to the mouth, excessive wear and tear, and congenital defects. Patients who have lost teeth are often reluctant to smile or talk. Additionally, biting irregularities caused by tooth loss can have a negative effect on eating habits. This can lead to secondary health problems, such as malnutrition.

Regardless of the nature of problems related to tooth loss, dental implants may provide a simple remedy with proven results. Dental implants are prosthetic (i.e., artificial) tooth replacements that are used to counter tooth loss. Dental implants are stronger and more durable than their restorative counterparts (i.e., dentures), and offer a permanent solution to tooth loss. Additionally, implants may be used in conjunction with other restorative procedures for maximum effectiveness. For example, a single implant can serve to support a crown replacing a single missing tooth. Implants can also be used to support a dental bridge for the replacement of multiple missing teeth, and can be used with dentures to increase stability and reduce gum tissue irritation.

Dental implant stents and other devices presently used by surgeons to place dental implants in a patient's mouth do not have features that allow the surgeons to place a dental implant parallel to other implants and/or existing teeth and at precise, predetermined depths within the arch of the mandible or maxilla. A similar drawback occurs with dental implants used as supporting members for the development of a dental prosthesis. When dental implants are not placed parallel to other dental implants, final restoration prostheses are much more difficult to manufacture and the fit and longevity of a final restoration is reduced.

Present surgical dental implant stents also lack features that allow surgeons to place a dental implant at a predetermined depth decided upon by the surgeon or allow a dental lab technician to manufacture a surgical dental implant stent that can be used to fabricate the final dental implant restoration that will be reliably retained in the patient's mouth. When surgeons have no means to accurately form an aperture to place a dental implant at a predetermined depth, the surgeons when making this aperture may pass through the bone of the mandible or maxilla, necessitating the location of a new site as well as restoring the damaged area. This often increases the amount of time required for the patient to heal and recover from the procedure.

Current surgical dental implant stents also lack features that would allow a surgeon to immediately place a final dental implant restoration. In fact, current dental implant stents normally take weeks to complete due to the trial-and-error fabrication process inherent to present systems. There is a need for a way to more accurately position oral implants in a patient's mouth and to reduce the amount of time required to produce and install them.

SUMMARY

An oral implant system and method are disclosed according to an embodiment of the present invention. The system comprises a positioning tool, a transfer band, a transfer screw and a transfer drill, all used in cooperation to provide for the accurate placement of a dental implant parallel to other implants and or existing teeth and at predetermined depths. Impressions are made of the patient's mouth and a model is made of the patient's maxilla and mandible. The model is marked for implant position, depth and size on either the maxilla or the mandible. Apertures are drilled into the model using the positioning tool, then analogs are installed into the model using the positioning tool and a surveyor. A final restoration prosthetic is then fabricated. Transfer bands are coupled to the analogs with transfer screws and a lower surgical stent portion conforming to the patient's mandible is fabricated. An upper surgical stent portion conforming to the patient's maxilla is also fabricated. The finished surgical stent, comprising the lower and upper stent portions, is fitted to the patient's occlusion and secured. A transfer drill is rotated and slidably inserted through chamfered openings in the transfer bands to drill apertures into the patient's maxilla or mandible as appropriate, the apertures having a predetermined position and depth. Implants are installed into the apertures and the surgical stent is removed. Finally, the final restoration prosthetic is secured to the implants.

One embodiment of the present invention may be an oral implant placement system comprising a surgical stent having a first portion and a detachable second portion, the first and second portions being sized and shaped to conform to an occlusion in a select region of a patient's mouth. At least one generally cylindrical transfer band is embedded in the first surgical stent portion, the transfer band having first and second opposing generally planar ends and an opening extending between the ends, the opening including an interior chamfer proximate the second end. The system may include a transfer drill having a chamfered shank portion sized and shaped to be slidably received by the opening of the transfer band. The surgical stent is positioned in the patient's mouth in conformance with the occlusion and the first surgical stent portion is secured, the second planar end of the transfer band being adjacent the region of the patient's mouth selected for the installation of a dental implant. The second surgical stent portion is detached after the first surgical stent portion is secured. The transfer drill is rotated and slidably inserted into the opening of the transfer band to drill an aperture in the region of the patient's mouth selected for the installation of a dental implant, the location, orientation and depth of the aperture being controlled by the chamfered shank of the transfer drill in cooperation with the mating interior chamfer of the transfer band. Finally, an implant is installed into the aperture at the predetermined location, orientation and depth.

Another embodiment of the present invention may be a method for placing an oral implant. The method may include the steps of sizing and shaping a first portion and a second portion of a surgical stent to conform to an occlusion in a select region of a patient's mouth. At least one generally cylindrical transfer band is embedded in the first surgical stent portion, the transfer band having first and second opposing generally planar ends and an opening extending between the ends, the opening including an interior chamfer proximate the second end. A transfer drill is provided, the transfer drill having a chamfered shank portion sized and shaped to be slidably received by the opening of the transfer band. The surgical stent is positioned in the patient's mouth in conformance with the occlusion and securing first surgical stent portion, the second planar end of the transfer band being adjacent the region of the patient's mouth selected for the installation of a dental implant. The second surgical stent portion is detached after the first surgical stent portion is secured. The transfer drill is rotated and slidably inserted into the opening of the transfer band to drill an aperture in the region of the patient's mouth selected for the installation of a dental implant, the location, orientation and depth of the aperture being controlled by the chamfered shank of the transfer drill in cooperation with the mating interior chamfer of the transfer band. Finally, an implant is installed into the aperture at the predetermined location, orientation and depth.

BRIEF DESCRIPTION OF THE DRAWINGS

Further features of the inventive embodiments will become apparent to those skilled in the art to which the embodiments relate from reading the specification and claims with reference to the accompanying drawings, in which:

FIGS. 3A and 3B are side and end views respectively of a positioning tool according to an embodiment of the present invention;

FIGS. 12A and 12B are side and end views respectively of a transfer drill according to an embodiment of the present invention;

DETAILED DESCRIPTION

Figure 1:
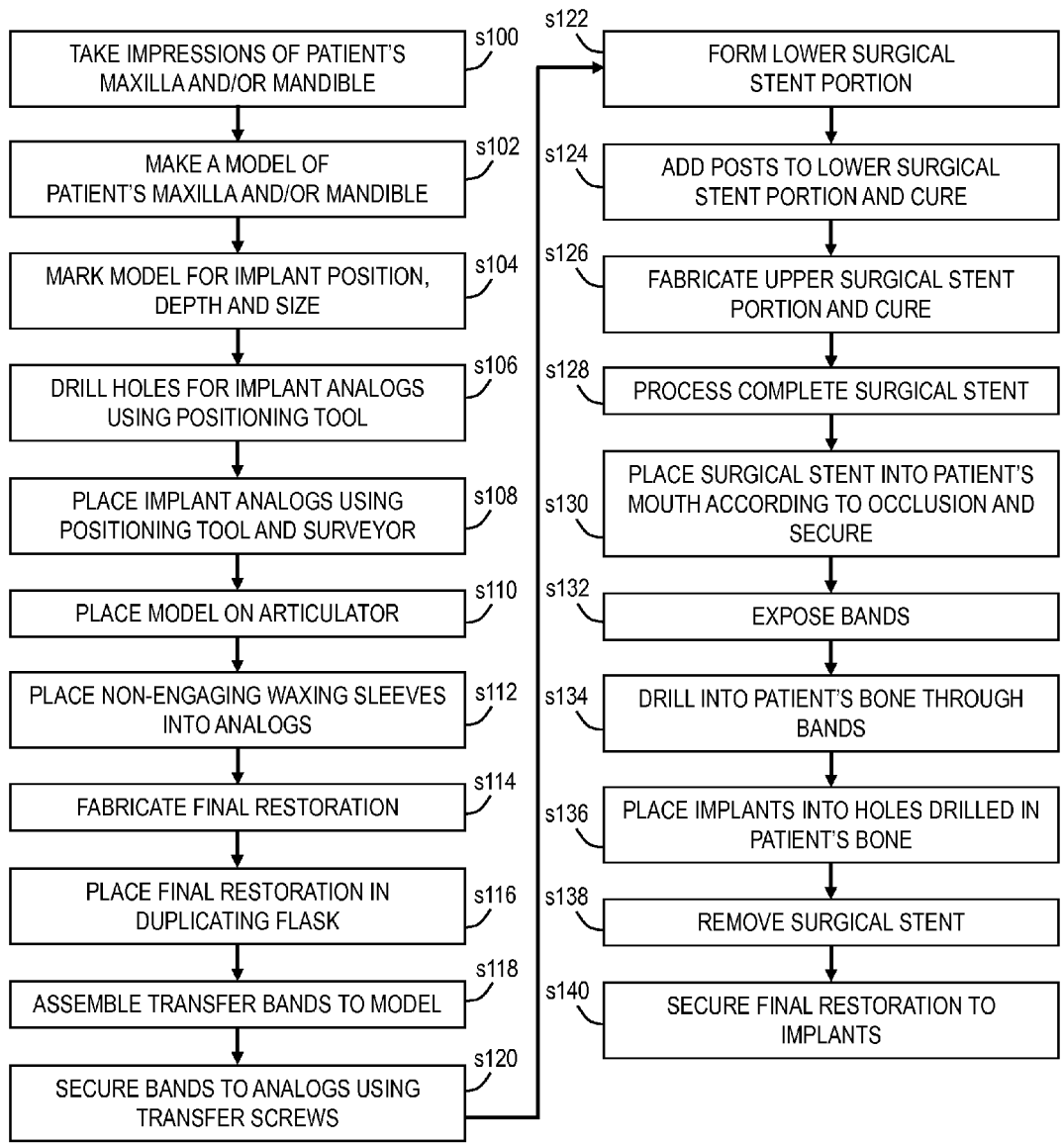
FIG. 1 is a flow diagram showing a process for making and installing oral implants according to an embodiment of the present invention.

The general arrangement of a process for producing an oral implant is shown in FIG. 1. Reference should be made to this figure in combination with other figures referred to in the discussion that follows.

At step s100 a set of impressions are made of the maxilla and/or mandible of a patient's mouth, particularly the patient's dental arch in the region of the patient's mouth selected for the installation of one or more dental implants. The object of making an impression is to accurately relate an analog of the implant or implant abutment to other structures in the dental arch. A malleable impression material is typically pressed into a tray, and the tray is then inserted in the patient's mouth. The patient bites into the impression material to create an impression of his or her maxilla and/or mandible in the material. Typical impression materials may include, without limitation, alginate, polyvinyl and rubber.

Figure 2:
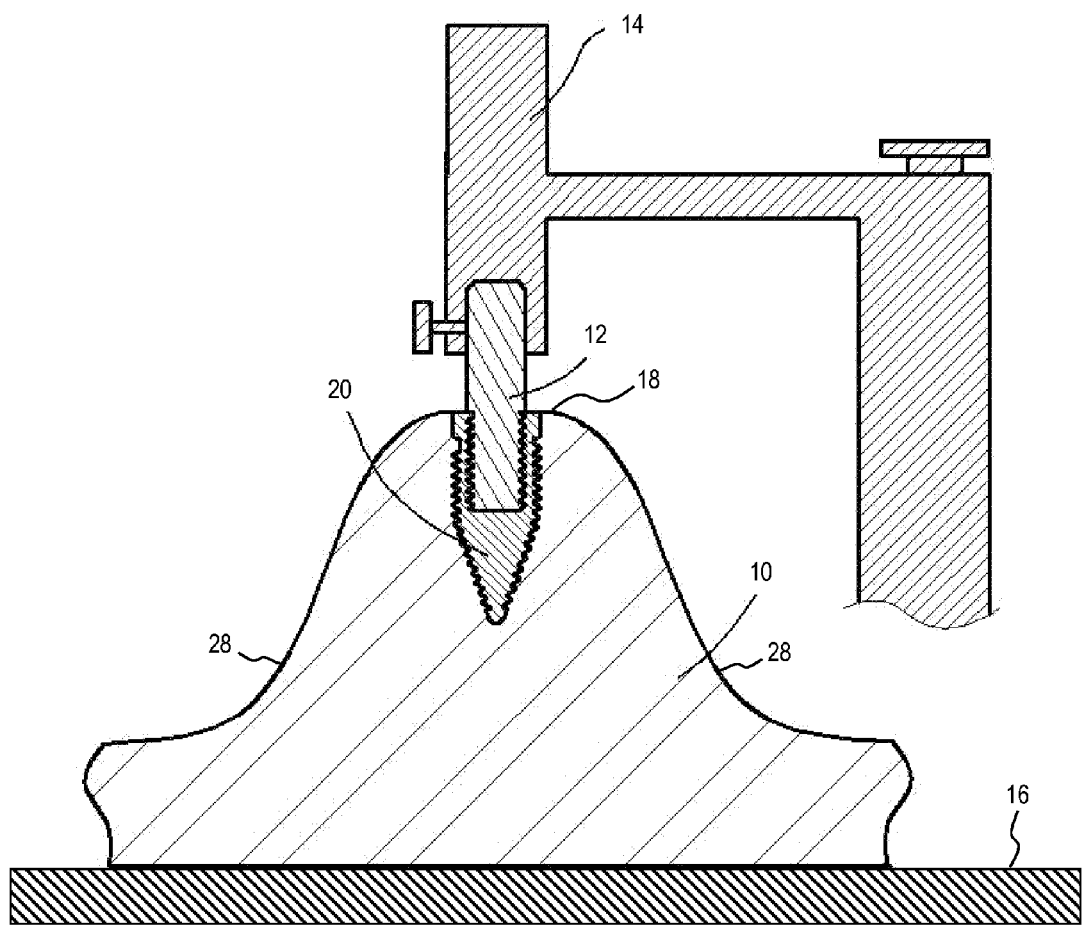
FIG. 2 is a view in section of a dental implant analog placed in a stone model according to an embodiment of the present invention.
Figure 4A:
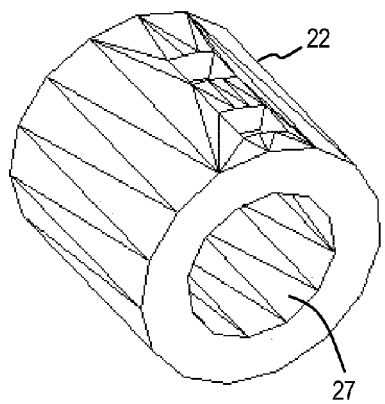
FIGS. 4A, 4B, 4C and 4D are isometric, end, side and sectional views respectively of a transfer band according to an embodiment of the present invention.
Figure 4B:
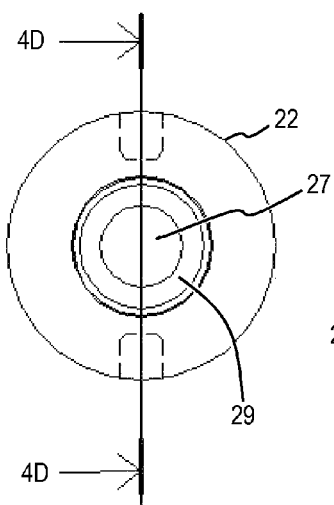
Figure 4C:
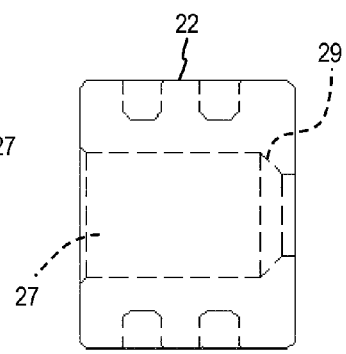
Figure 4D:
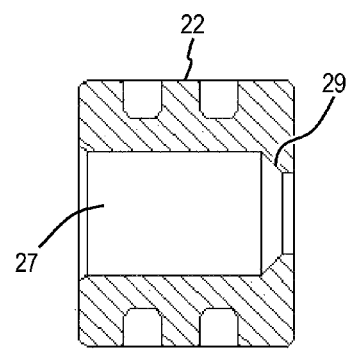
Figure 5A:
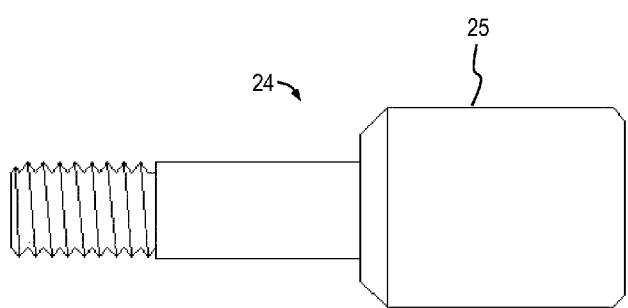
FIGS. 5A, 5B and 5C are side, end and sectional views respectively of a transfer screw according to an embodiment of the present invention.
Figure 5B:
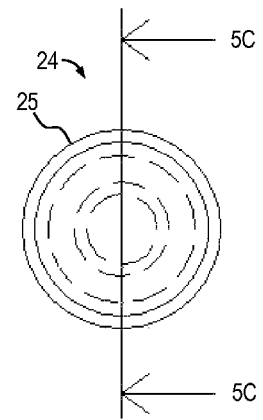
Figure 5C:
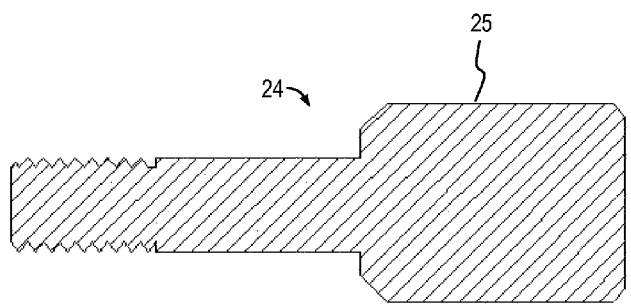

With reference to FIG. 2, at step s102, after the impression material sets it is used as a mold to form a laboratory stone dental model 10 of the patient's mouth by pouring plaster or the like into the mold, which hardens and sets to form a model of the patient's maxilla and/or mandible. Once hardened the model 10 is marked to indicate the position, depth and size of the implant, as at step s104.

With reference to FIGS. 2, 3A and 3B together, a positioning tool 12 is installed into a conventional dental surveyor 14. The marked stone model 10 is then placed onto a level surveyor's table 16 such as the type used in making dental "partials" and a ridge 18 of the model (which represents the patient's dental arch) is oriented generally level with respect to the surveyor's table. At step s106 holes are drilled into ridge 18. Implant analogs 20 are marked for the appropriate depth, then installed into model 10 such that the surface of ridge 18 is generally even with the mark, as at s108. By using surveyor 14 and positioning tool 12 as a tooling fixture implant analogs 20 can be placed into model 10 and oriented in parallel with each other with relative precision. As can be seen in FIG. 2, interior threads of analogs 20 are matingly coupled to exterior threads of positioning tool 12, the positioning tool and surveyor 14 cooperating to control the placement of the analogs to a predetermined location, orientation and depth within model 10.

At step s110 model 10 is placed on a conventional dental articulator (not shown) configured to hold the model. The articulator is adjusted for the characteristics of the patient's mouth and provides a mechanical means to duplicate the patient's jaw movements and teeth.

Figure 16:
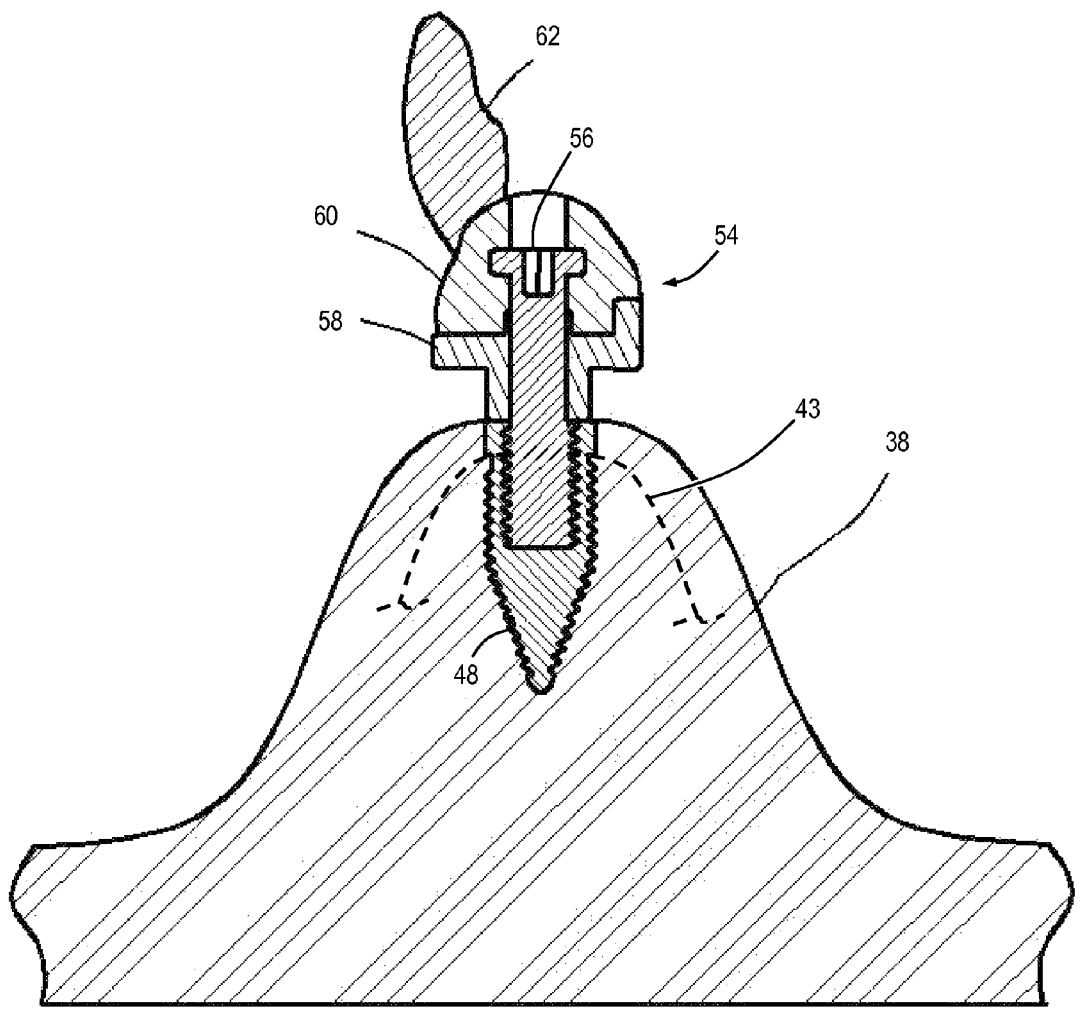
FIG. 16 shows a final restoration prosthetic joined to the implant of FIG. 15.

With continued reference to FIG. 2, at step s112 conventional waxing sleeves (not shown) are screwed into the interior threads of analogs 20 after removal of positioning tool 12 therefrom. At step s114 a final restoration is fabricated using a conventional lost-wax technique wherein a wax or acrylic bar is made using the waxing sleeves. The wax or acrylic bar is used to cast a metal bar, such as at 58 (FIG. 16). Acrylic prosthetic teeth appropriate for the implant are waxed to the metal bar. The wax is then processed to acrylic using a conventional lost-wax process, completing the final restoration prosthetic.

At step s116 the final restoration prosthetic is placed into a conventional dental duplicating container or "flask" (not shown). Dental flasks are used in the production of permanent dental parts which are fixedly retained in the mouth, such as implants. The dental parts are typically are made from acrylic resins, such as methyl methacrylate polymers or copolymers. The acrylic resin is processed in brass flasks for compression molding of the acrylic resin into the desired configuration of the prosthetic dental device while the acrylic resin is in a putty or dough-like stage. The final restoration prosthetic is duplicated and saved for later use.

Figure 6:
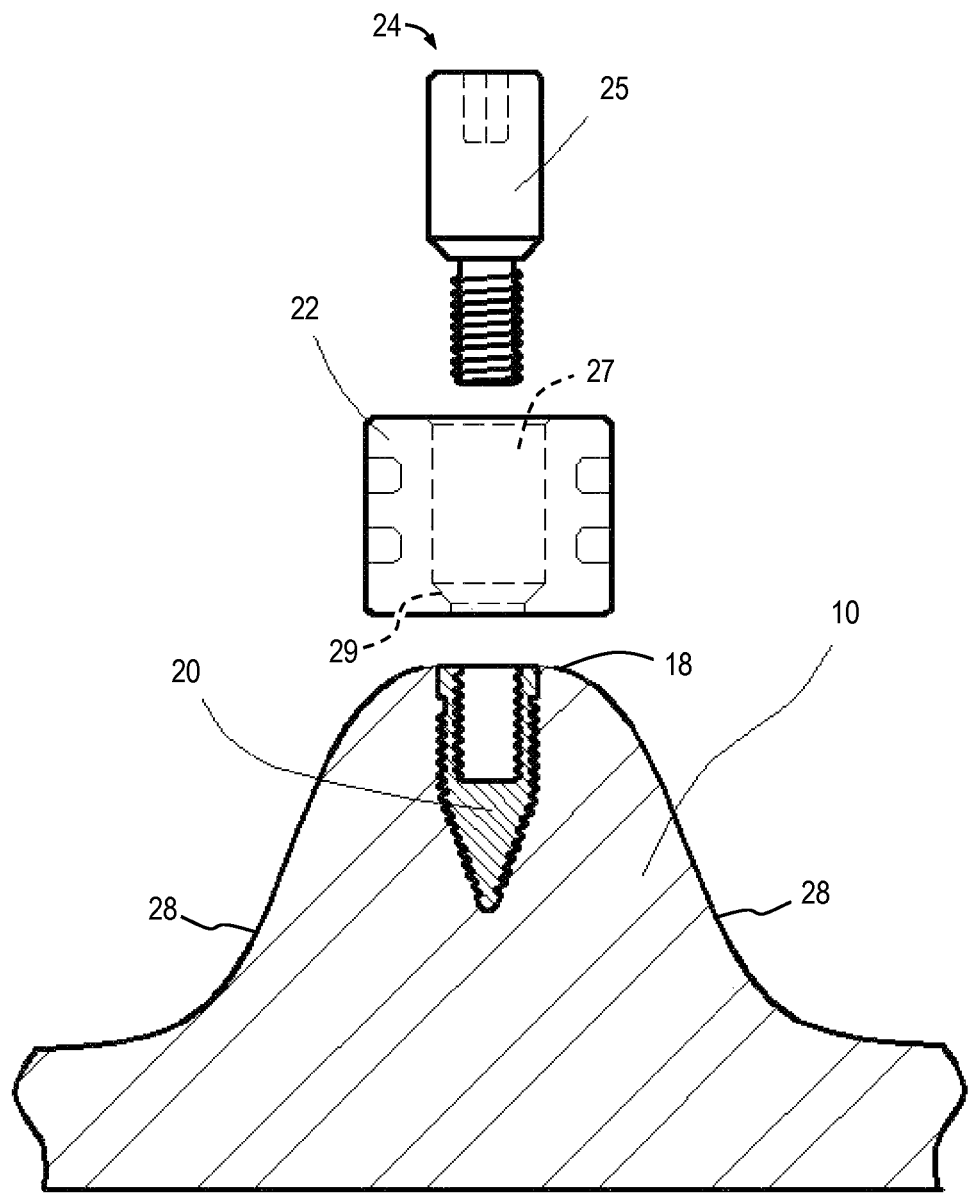
FIG. 6 shows the transfer band of FIGS. 4A, 4B, 4C and 4D being assembled to an analog set into a model with the transfer screw of FIGS. 5A, 5B and 5C according to an embodiment of the present invention.
Figure 7:
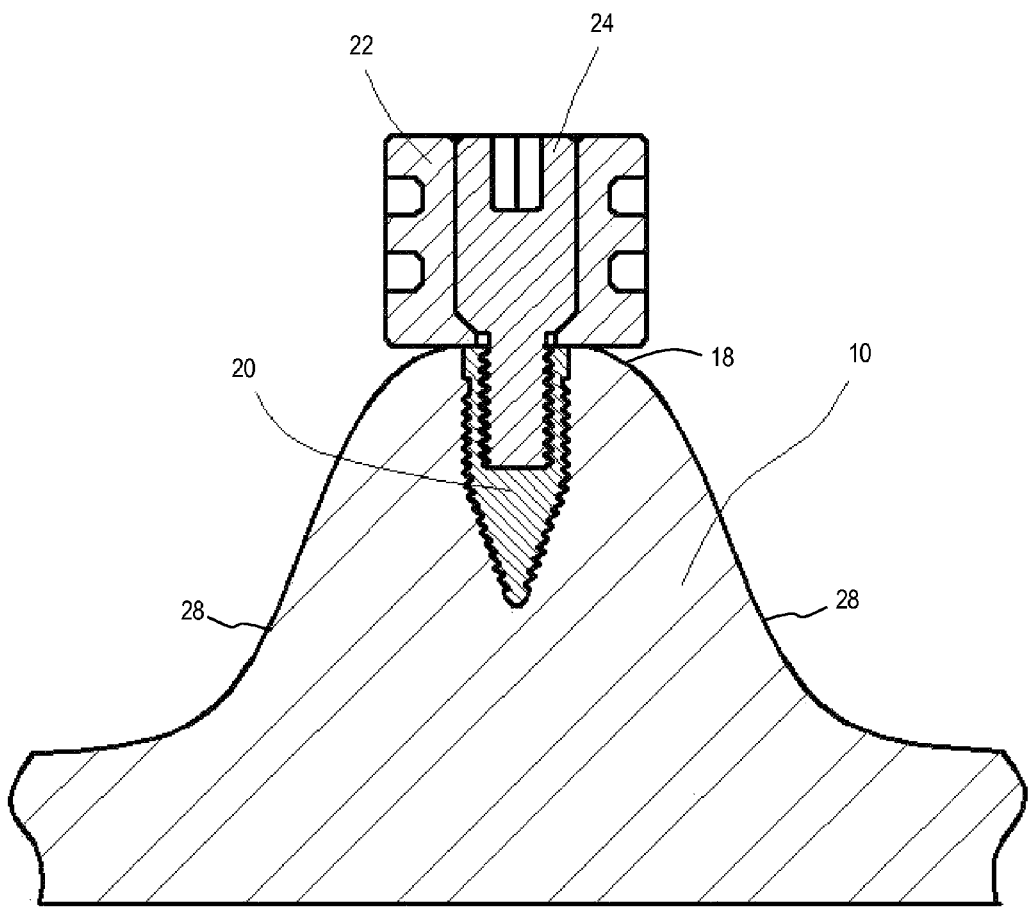
FIG. 7 shows the components of FIG. 6 in an assembled condition.

With reference to FIGS. 4A-4D, 5A-5C, 6 and 7 together a transfer band 22 is assembled to each of analogs 20 with a transfer screw 24 at step s118, as shown in FIG. 6. Each transfer band 22 is secured to a corresponding analog 20 with a transfer screw 24 at step s120, as shown in FIG. 7, a chamfered shank portion 25 of the transfer screw being received by an opening 27 of the band until it mates with a chamfered portion 29 within the band.

Figure 8:
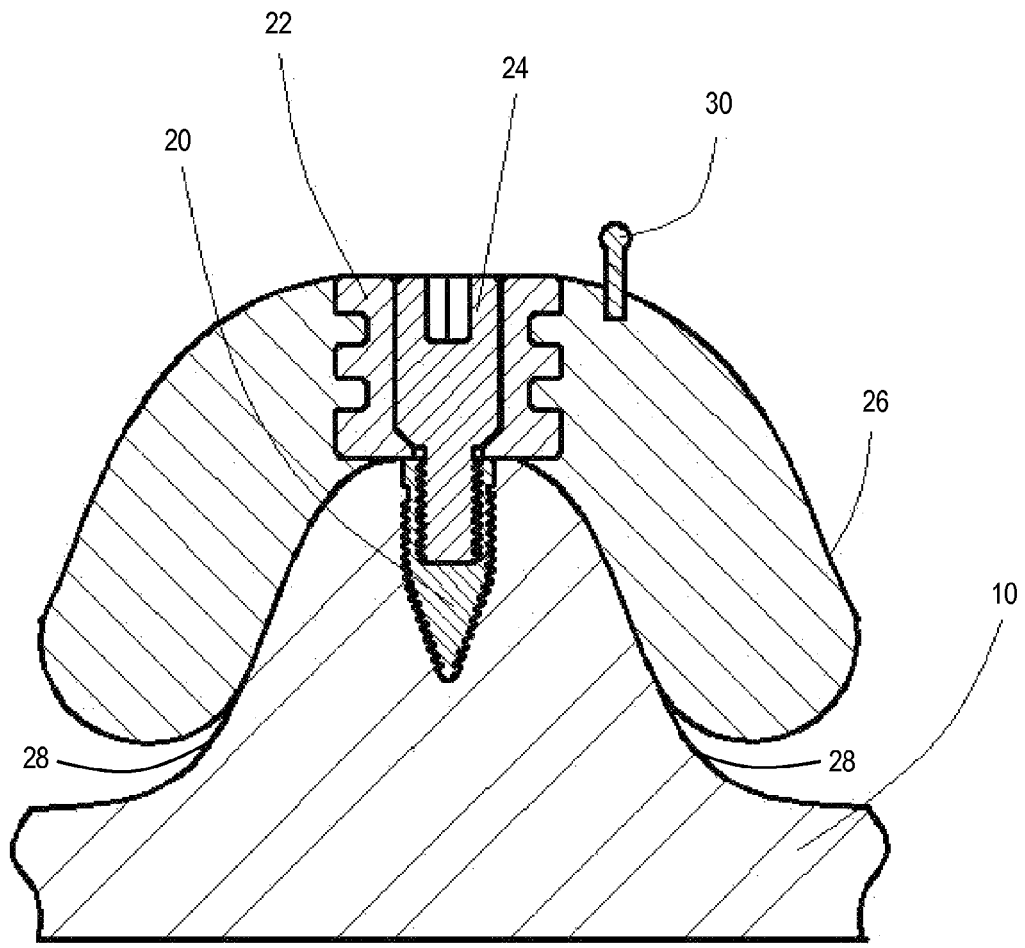
FIG. 8 shows details of a lower portion of a surgical stent according to an embodiment of the present invention.

With reference to FIG. 8, at step s122 a malleable acrylic material is applied to model 10 to form a lower surgical stent portion 26, the acrylic material covering bands 22. Lower surgical stent portion 26 preferably covers substantially all of ridge 18 of model 10, extending proximate a set of peripheries 28 of the model.

At step s124 a pair of posts 30 are installed into acrylic material of lower surgical stent portion 26, as shown in FIG. 8. The acrylic material of lower portion 26 is then hardened using any process appropriate to the select material, such as baking and light-curing with ultraviolet (UV) or visible light.

Figure 9:
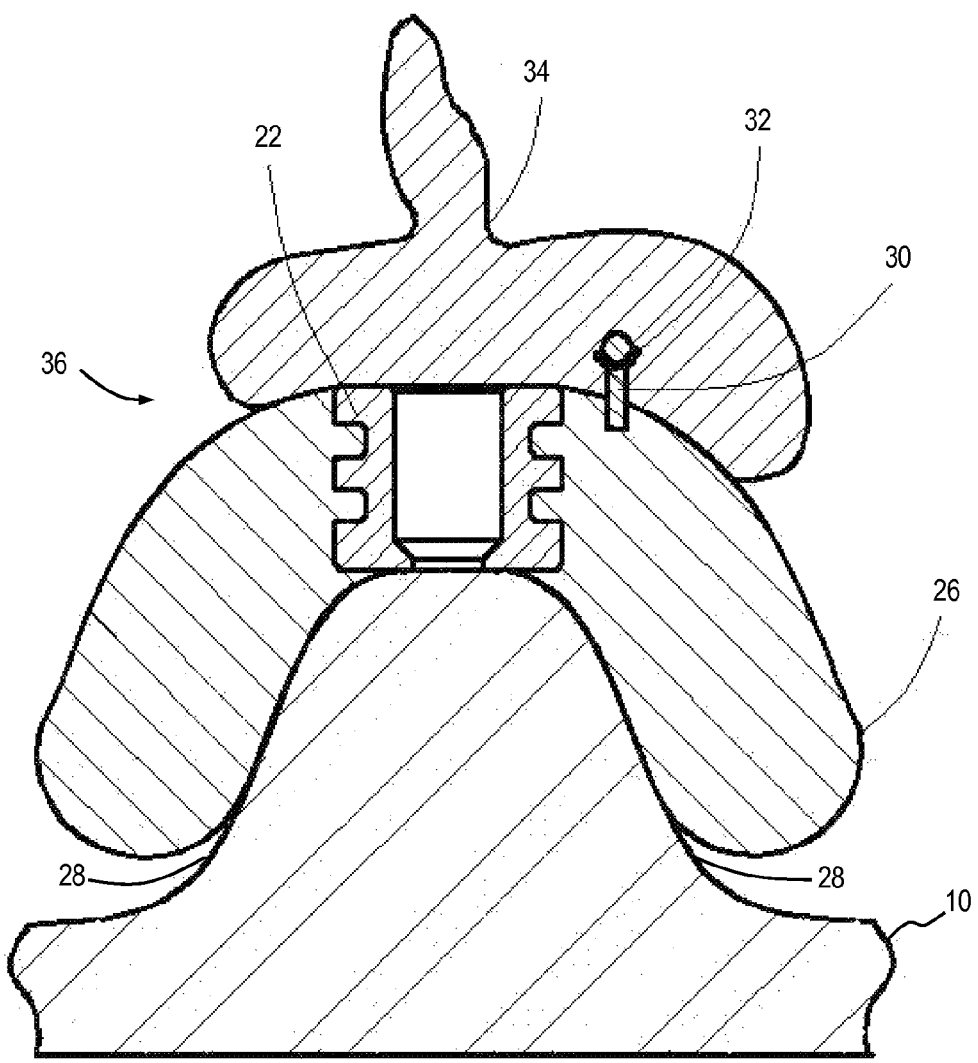
FIG. 9 shows details of an upper portion of a surgical stent according to an embodiment of the present invention.

With reference to FIG. 9, at step s126 transfer screws 24 are removed from bands 22 and "O-rings" 32 are placed onto posts 30. Then, using the dental duplicating flask of step s116 and the impressions of steps s100 and s102 a pourable or cold-cure acrylic material is applied to lower surgical stent portion 26, forming an upper surgical stent portion 34 opposing the lower portion. That is, if lower surgical stent portion 26 represents the patient's maxilla, upper surgical stent portion 34 represents the patient's mandible and vice versa. Together, lower portion 26 and upper portion 34 form an accurate representation of the patient's occlusion in the region of the patient's mouth selected for the installation of one or more dental implants. The acrylic material of upper surgical stent portion 34 is then hardened using any process appropriate to the select material, such as cold-curing, forming the complete surgical stent 36 of step s128. Lower surgical stent portion 26 and upper surgical stent portion 34 are detachably coupled together by posts 30, which also serve as registration points aiding to align the lower and upper surgical stent portions.

Figure 10:
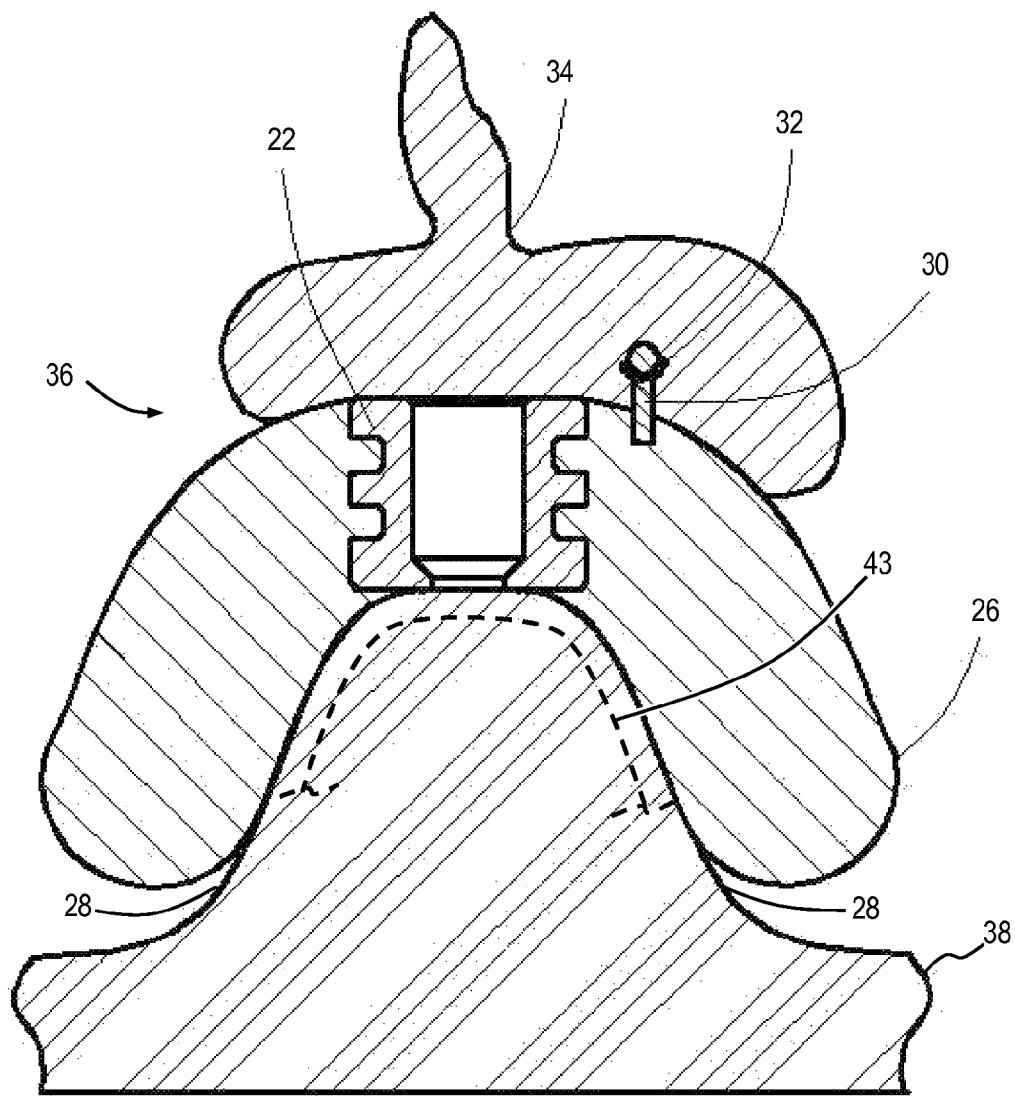
FIG. 10 shows the lower and upper surgical stent portions of FIGS. 8 and 9 placed in the mouth of a patient according to an embodiment of the present invention.
Figure 11:
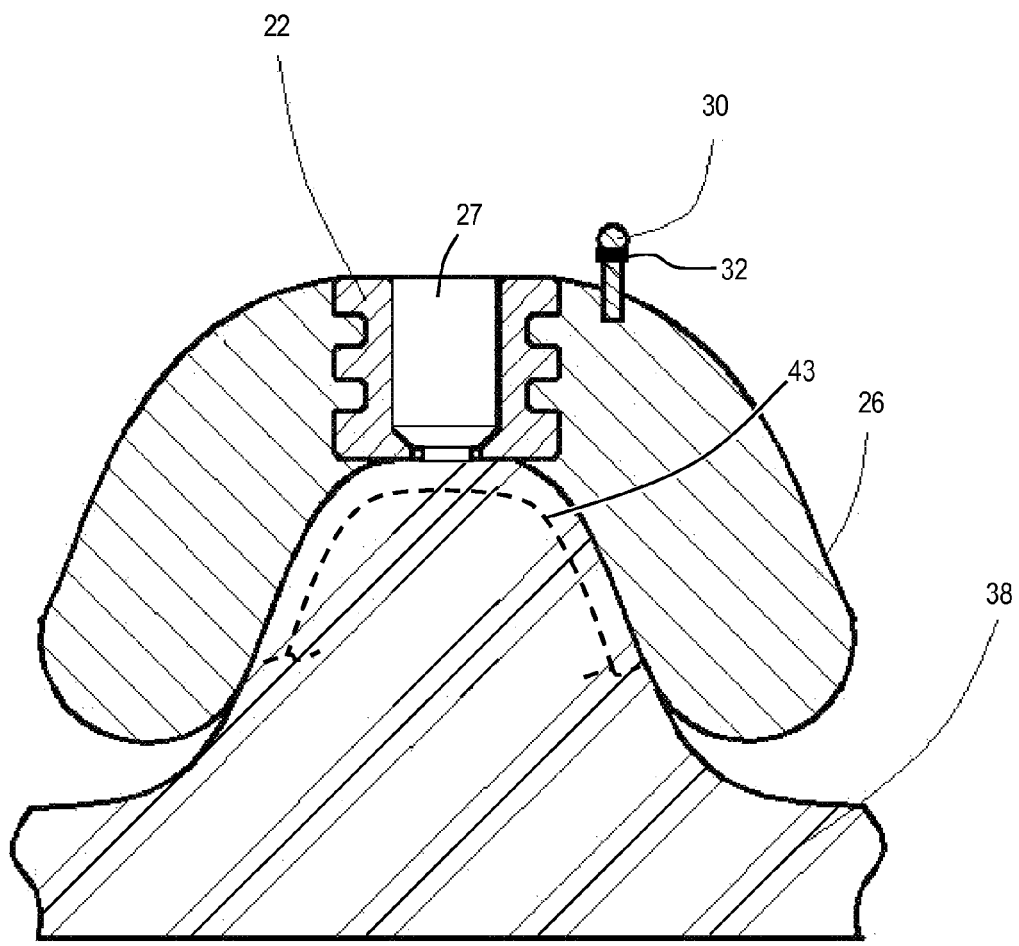
FIG. 11 shows the stent of FIG. 10 with the upper stent portion removed.

With reference to FIG. 10, at step s130 surgical stent 36 is placed into the mouth 38 of the patient, aligned according to the patient's occlusion, and secured to the patient's maxilla and/or mandible in any desirable manner, such as sutures. Once stent 36 is secured upper portion 34 is detached from lower portion 26, exposing transfer bands 22, as at step s132 and shown in FIG. 11.

Figure 13:
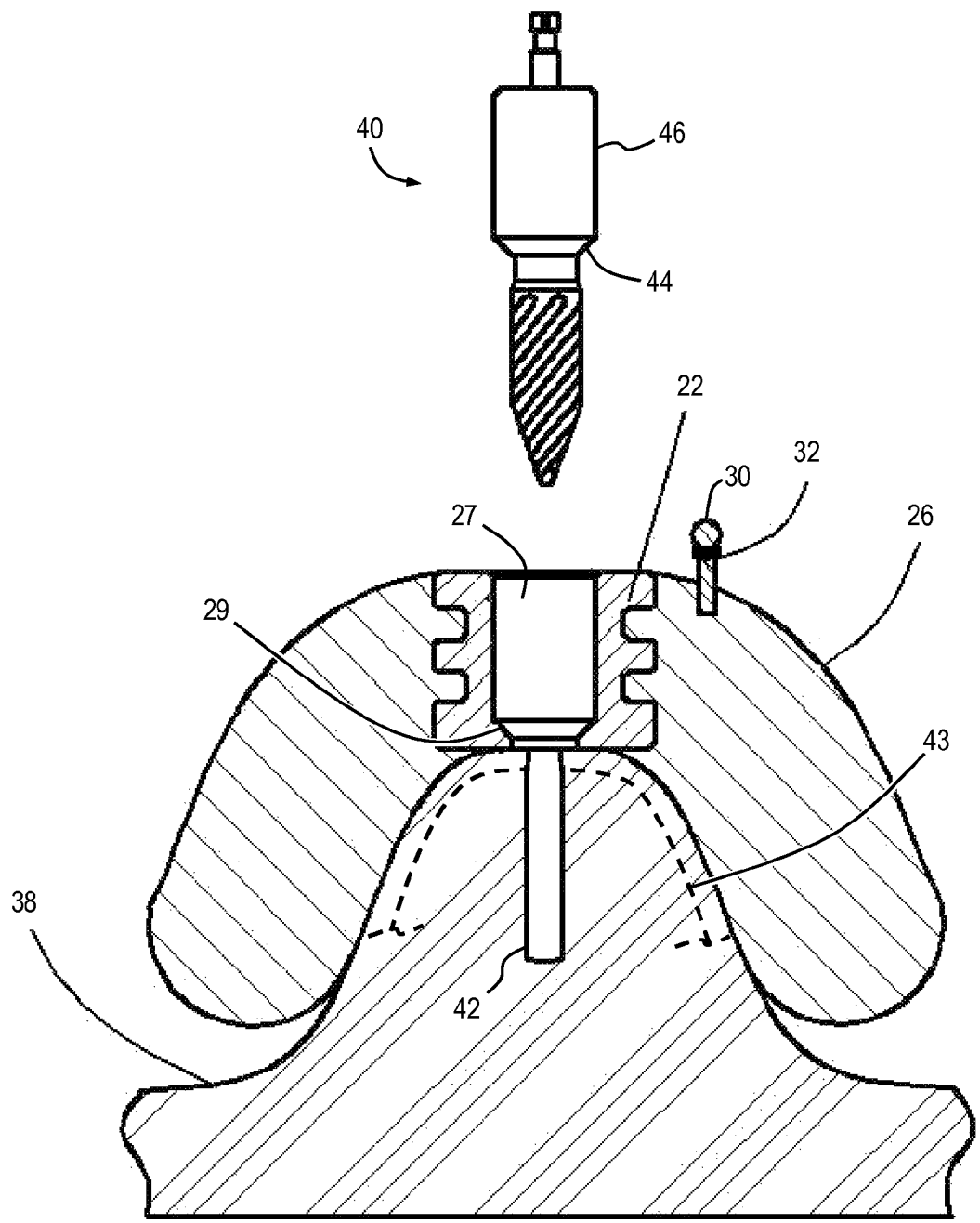
FIG. 13 shows an aperture being drilled into a bone structure of a patient according to an embodiment of the present invention.

With reference to FIGS. 12A, 12B and 13, at step s134 a transfer drill 40 is rotated and slidably inserted into opening 27 of transfer band 22 to drill an aperture 42 into the patient's bone 43. The position and the depth of the transfer drill's penetration into bone 43 is controlled by chamfered portion 29 of opening 27 of transfer band 22, which corresponds to the size and shape of a chamfered portion 44 of a shank 46 of the transfer drill 40. This process is repeated for each transfer band 22. Although a particular embodiment of transfer drill 40 is shown in FIGS. 12A and 12B various sizes, shapes and forms of transfer drills having a chamfered portion 44 of a shank 46 are envisioned within the scope of the invention.

Figure 14:
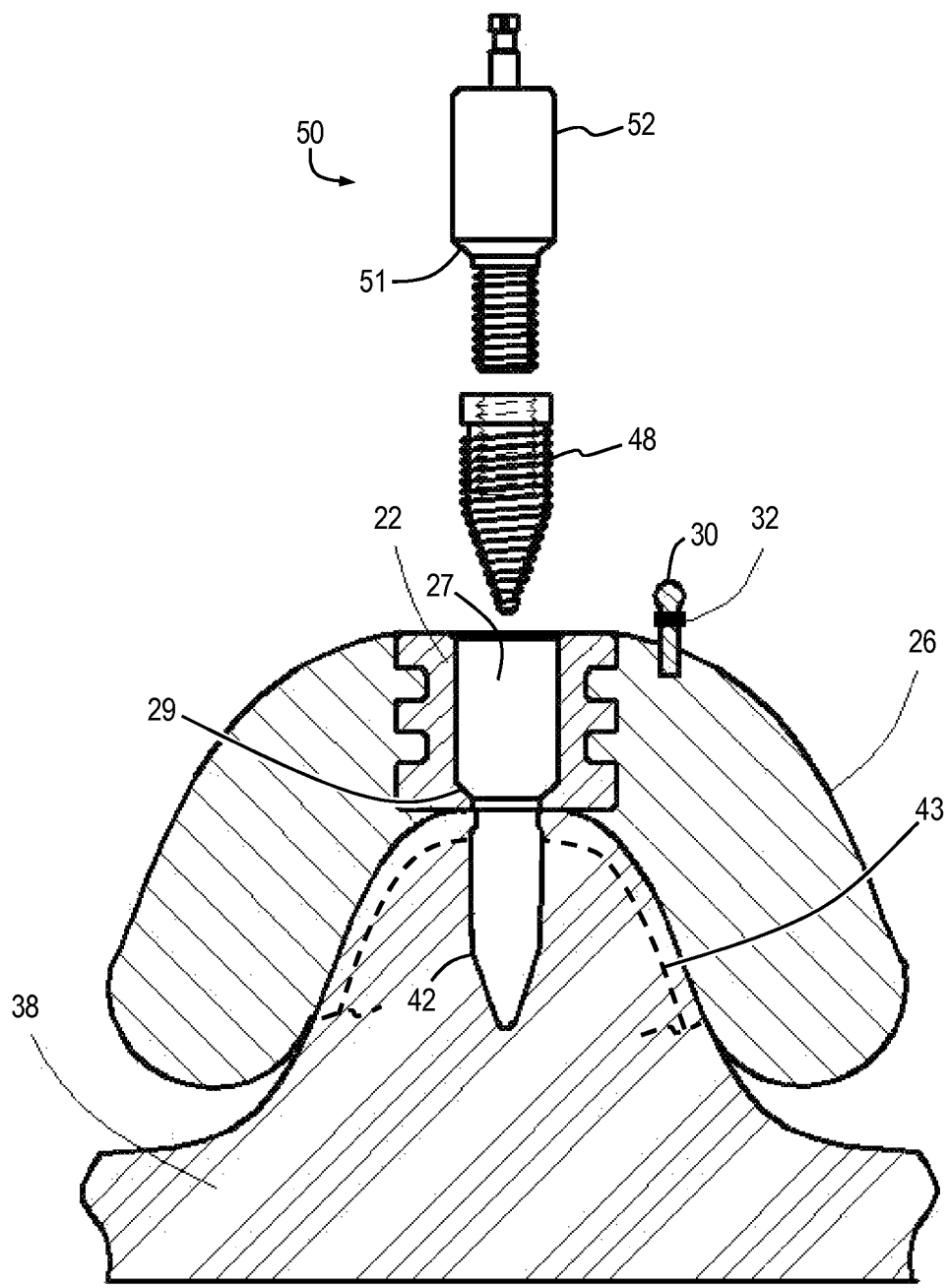
FIG. 14 shows an implant being installed into the aperture of FIG. 13 according to an embodiment of the present invention.
Figure 15:
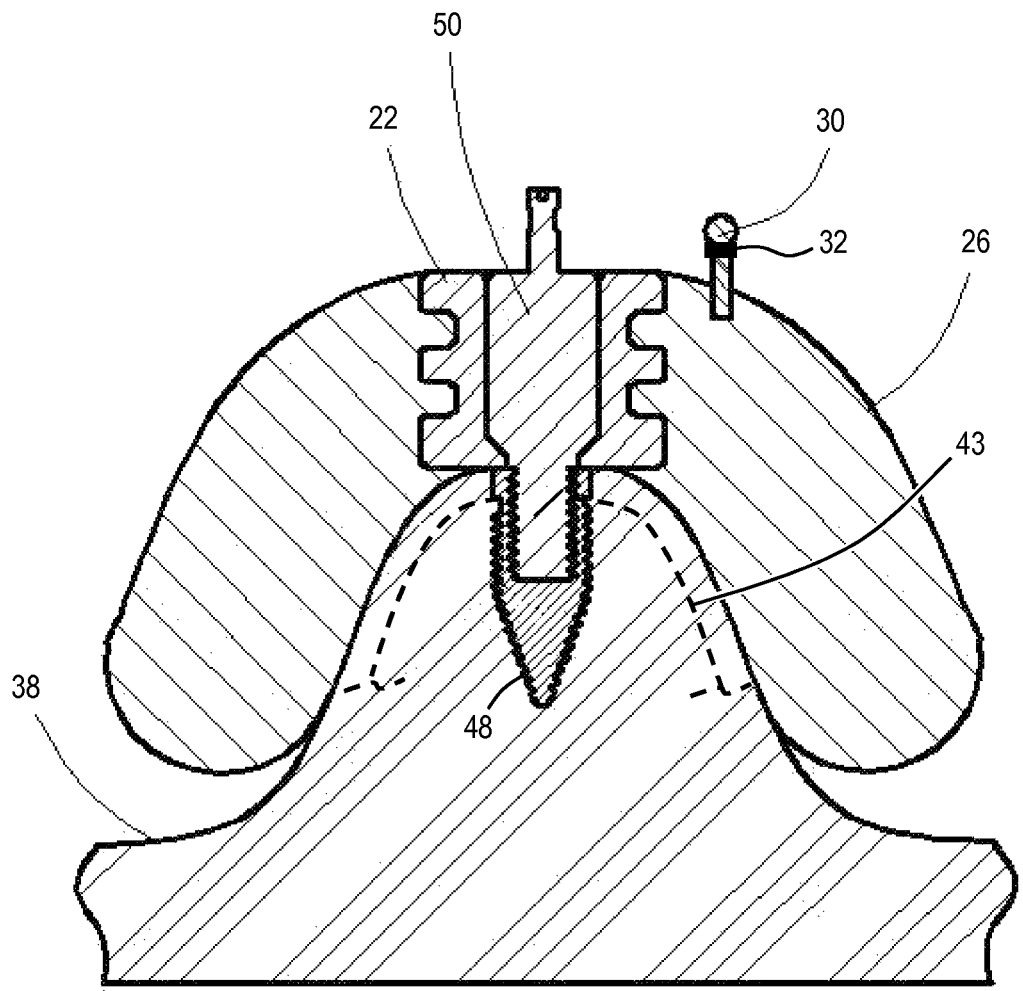
FIG. 15 shows the implant of FIG. 14 in an installed condition.

With reference to FIGS. 14 and 15, at step s136 a conventional implant 48 is installed into bone 43 through aperture 42 using a corresponding conventional placement appliance 50, external threads of the placement appliance being coupled to internal threads of the implant. The location, orientation and depth of the implant 48 with respect to bone 43 of mouth 38 is controlled by chamfered portion 29 of opening 27 of transfer band 22, this chamfered opening corresponding to the size and shape of a chamfered portion 51 of a shank 52 of the placement appliance 50. Once all of implants 48 are installed into corresponding apertures 42 lower portion 26 is removed at step s138.

With reference to FIG. 16, at step s140 the final restoration 54 is coupled to implants 48 and secured thereto with implant screws 56 extending through the final restoration and into the implants. As also shown in FIG. 16, final restoration 54 comprises a bar 58, an acrylic base portion 60 and prosthetic teeth 62.

In some embodiments of the present invention any or all of transfer band 22, transfer screw 24 and transfer drill 40 may have identifying marks indicating particular characteristics, such as size and drilling depth, among others. The identifying marks may be one or more of lettering, numbering, symbols and colors. The identifying marks enable a user to match up compatible transfer bands 22, transfer screws 24 and transfer drills 40 for a given implantation procedure.

As previously noted, the surgical stent 36 comprises lower surgical stent portion 26 and upper surgical stent portion 34, the lower and upper surgical stents conforming to the patient's lower and upper dentition (maxilla and/or mandible). Accordingly, the patient's occlusion can be precisely matched with the result that the final restoration prosthetic 54 ultimately coupled to the installed implants 48 will likewise be precisely matched to the occlusion.

An important advantage of the present invention is the ability to provide an "immediate load" of final restoration prosthetic 54. That is, final restoration prosthetic 54 may be coupled to implants 48 immediately after the implants are installed. This procedure is preferable to current methods which typically require a number of procedures and medical office visits, which are both time-consuming and inconvenient for the patient. Of course, one skilled in the art will recognize that the final restoration prosthetic 54 may be coupled to implants 48 some time after the implants are installed and the post-operative healing process is underway or complete, as may be preferable to some dental practitioners.

It should also be noted that the system and method described herein is scalable. Thus, final restoration prosthetic 54 may comprise a single prosthetic tooth 62, a bridge comprising several prosthetic teeth or even a complete appliance replacing all the teeth of the maxilla or mandible.

The foregoing discussion primarily addresses the installation of implants 48 into the mandible of a patient. However, it will be understood by those skilled in the art that the process is equally applicable to the installation of implants 48 into the maxilla, within the scope of the invention.

While this invention has been shown and described with respect to a detailed embodiment thereof, it will be understood by those skilled in the art that changes in form and detail thereof may be made without departing from the scope of the claims of the invention.

What is claimed is:

1. A method for placing an oral implant, comprising the steps of:

sizing and shaping a first portion and a separate, selectably detachable second portion of a surgical stent to conform to an occlusion comprising a select region of mandible and maxilla of a patient's mouth, wherein a post embedded in the first portion extends into the second portion;

embedding a generally cylindrical transfer band in the first surgical stent portion, the transfer band having first and second opposing generally planar ends and an opening extending between the ends, the opening including a chamfer proximate the second end;

providing a transfer drill having a chamfered shank portion sized and shaped to be slidably received by the opening of the transfer band;

positioning the surgical stent in the patient's mouth in conformance with the occlusion and securing the surgical stent, the second planar end of the transfer band being adjacent the region of the patient's mouth selected for the installation of a dental implant;

detaching the second surgical stent portion after the first surgical stent portion is secured;

rotating and slidably inserting the transfer drill into the opening of the transfer band to drill an aperture in the region of the patient's mouth selected for the installation of a dental implant; the location, orientation and depth of the aperture being controlled by the shank of the transfer drill in cooperation with the opening of the transfer band, the chamfer of the shank of the transfer drill meeting the chamfer of the transfer band at a predetermined depth; and installing an implant into the aperture at the predetermined location, orientation and depth.

2. The method of claim 1, further comprising the step of making a model from impressions of the patient's maxilla and mandible, the model having a size and shape conforming to the occlusion of the patient's mouth selected for the installation of a dental implant, the model being used to form the surgical stent.

3. The method of claim 2, further comprising the steps of:
providing a dental surveyor;
coupling a positioning tool to the dental surveyor;
coupling an implant analog to the dental surveyor to hold the implant analog at a predetermined location and orientation; and
installing the implant analog into the model to a predetermined depth.

4. The method of claim 3, further comprising the step of placing identifying marks on at least one of the positioning tool, transfer drill and transfer band, wherein the identifying marks indicating particular characteristics.

5. The method of claim 4, further comprising the step of coupling the analog to the model at a predetermined location, orientation and depth corresponding to the location, orientation and depth of the implant to be installed in the patient's mouth.

6. The method of claim 1, further comprising the step of embedding a second post in the first surgical stent portion and extending into the second surgical stent portion, the posts aiding to align the first and second surgical stent portions and further acting to detachably couple the first and second surgical stent portions together.

7. The method of claim 6, further comprising the step of coupling an O-ring to each of the posts.

8. The method of claim 1, further comprising the step of making the first and second surgical stent portions from an acrylic material.

9. The method of claim 8, further comprising the step of making the first surgical stent portion from a light-curable acrylic material.

10. The method of claim 8, further comprising the step of making the second surgical stent portion from a cold-curable acrylic material.

11. The method of claim 1, further including the step of securing the surgical stent with sutures.

12. The method claim 1, further including the step of coupling a final restoration to the implant.

13. The method of claim 12 wherein the final restoration comprises a single prosthetic tooth.

14. The method of claim 12 wherein the final restoration comprises a plurality of prosthetic teeth.

15. The method of claim 1 wherein the implant is installed into the patient's mandible.

16. The method of claim 1 wherein the implant is installed into the patient's maxilla.

* * * * *